(12) United States Patent
Sheffer et al.

(10) Patent No.: US 6,743,220 B2
(45) Date of Patent: Jun. 1, 2004

(54) GRASPER DEVICE FOR USE IN MINIMALLY INVASIVE SURGERY

(76) Inventors: Michael Sheffer, Hazorim 11, Givat Ella (IL), 23800; Arkadi Gorenstein, Mercaz Baali Melacha 21, Tel Aviv (IL), 63823

( * ) Notice: Subject to any disclaimer, the term of this patent is extended or adjusted under 35 U.S.C. 154(b) by 42 days.

(21) Appl. No.: 10/135,363

(22) Filed: May 1, 2002

(65) Prior Publication Data

US 2003/0208185 A1 Nov. 6, 2003

(51) Int. Cl.[7] .............................................. A61B 17/00
(52) U.S. Cl. .......................................... 606/1; 600/37
(58) Field of Search ................................................ 606/1

(56) References Cited

U.S. PATENT DOCUMENTS

| | | | |
|---|---|---|---|
| 5,951,490 A | * | 9/1999 | Fowler ........................ 600/571 |
| 6,394,948 B1 | * | 5/2002 | Borst et al. .................. 128/897 |
| 6,464,629 B1 | * | 10/2002 | Boone et al. .................. 600/37 |
| 6,558,382 B2 | * | 5/2003 | Jahns et al. .................... 606/41 |

* cited by examiner

Primary Examiner—Roy D. Gibson
Assistant Examiner—Henry M. Johnson, III
(74) Attorney, Agent, or Firm—Mark M. Friedman

(57) ABSTRACT

A surgical instrument for use by a surgeon for grasping a tissue of a surgical patient without causing a crush injury of the tissue is disclosed. The instrument includes an elongate shaft having two ends with a handle at a first end of the shaft, and a grasping tip at a second end of the shaft. The grasping tip includes a body housing at least one suction element, wherein the at least one suction element mechanically produces suction locally (distally) within the grasping tip.

26 Claims, 7 Drawing Sheets

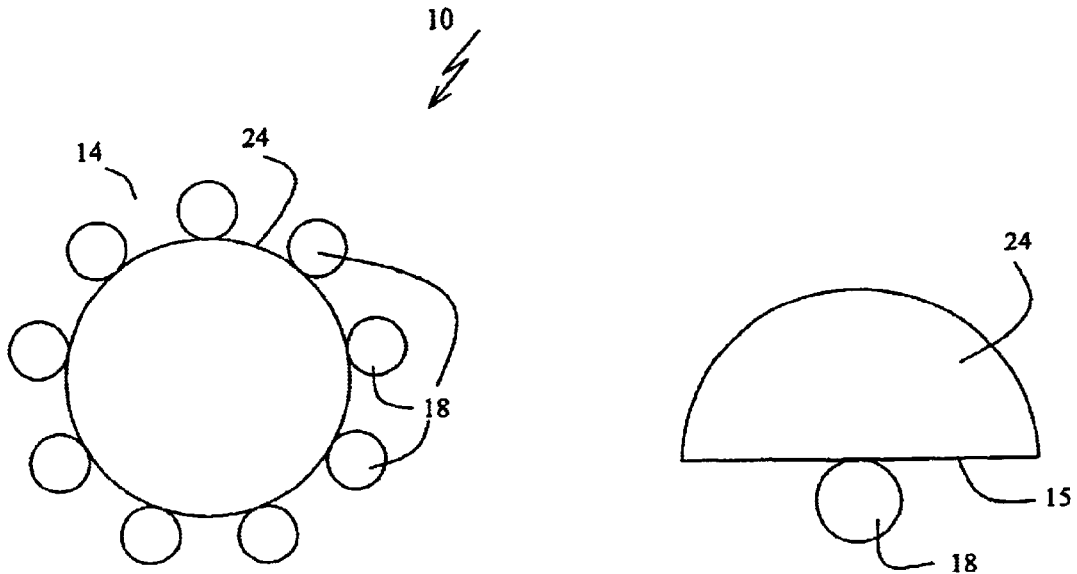
FIG. 1B
FIG. 1D
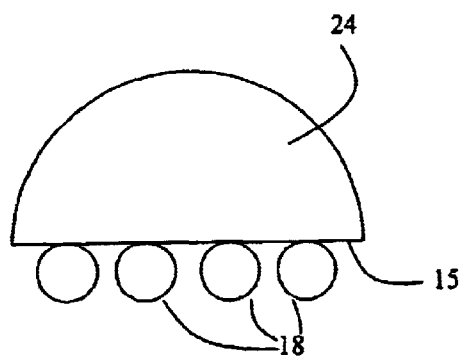
FIG. 1C

GRASPER DEVICE FOR USE IN MINIMALLY INVASIVE SURGERY

FIELD AND BACKGROUND OF THE INVENTION

The present invention relates to a surgical instrument and, more particularly, to a grasping device for use in minimally invasive surgery.

In recent years there has been an enormous growth in the number of surgical procedures being performed using laparoscopic techniques, best refereed to as minimally invasive surgery. This has been perhaps the most widely recognized surgical innovation since the development of anesthesia. Minimally invasive surgical procedures avoid the necessity of using large and traumatic surgical incisions into body cavities. Because minimally invasive surgery uses smaller incisions and involves less trauma it enables shorter hospital stays and a much faster surgical recovery with less pain and scarring. Minimally invasive surgery is used in all fields of surgery including general surgery, pediatric surgery, gynecology, cardio-thoracic surgery, urologic and others. For example, more than 95% of the 600,000 gallbladder operations performed each year in the U.S. are now done laparoscopically. A National Institutes of Health expert panel concluded that the laparoscopic approach to cholecystectomy is the "procedure of choice."

Although the specific surgical techniques employed vary among procedures and between different surgical subspecialties, all minimally invasive surgical procedures generally employ video-imaging systems in order to provide anatomic visualization within the region of the body being operated upon. Achieving such visualization requires the creation and maintenance of an optical cavity, typically created with carbon dioxide insufflation. In abdominal surgery for example, using short incisions in the skin, as opposed to the long wide incisions typically employed in conventional surgery, narrow tubes are inserted through the abdominal wall so that various instruments can be passed through them to perform the surgical maneuvers necessary for the operation. The various maneuvers are viewed directly on a monitor that receives its image from a video camera attached to the laparoscope. Various specialized surgical instruments are inserted through the small access "keyhole" incisions (access ports) in the skin and utilized within the established optical cavity for the removal or repair of an organ.

One of the most basic needs required by minimally invasive surgery is the need to grasp and move adjacent tissues from the tissues on which they abut. These displaced tissues themselves often require surgical treatment upon them. Thus specific instruments are required that allow grasping, holding, manipulation and movement of organs and tissues, through small access port incisions, often in an insufflated body cavity, under endoscopic guidance. The conventionally used grasper is a forceps-like device which has the significant limitation that use of this device causes mechanical, physical trauma to the tissue or organ being grasped or taken hold of. Many of the tissues that require manipulation are delicate and very vulnerable to such mechanical damage of crush injury from the point pressure of the forceps jaws, such as is encountered during removal of tumors from the liver, manipulation of the ovaries and fallopian tubes or operation on kidney tissue. Further, these conventional devices generally have a scissors like handle making its shape uncomfortable for the surgeon to hold and use. Further the entire device needs to be sterilized after each procedure.

In order to avoid the mechanical trauma associated with the conventional forceps type grasper, several devices have been proposed that use vacuum suction for taking hold of the tissue to which the instrument has been applied. For example, U.S. Pat. No. 5,196,003 to Bilweis describes a surgical instrument, in particular for endoscopic surgery, which includes a tube with a suction cup at one end, and a bulb at the other, such that the volume of the bulb is in communication with the suction cup via the tube in order to enable the suction cup to be applied against and adhere to tissues or organs for displacement under the control of suction from the bulb. U.S. Pat. No. 5,799,661 to Boyd et al. describes a suction cup retractor has an elongated tubular shaft having a suction cup shaped manipulator at the distal end. A vacuum lumen extends through the tubular shaft and the proximal end is adapted for attachment to a vacuum source.

Both of these suction retractors suffer from significant limitations. The relatively large suction cup head exerts a high suction pressure on the tissue to which it is applied making the device liable to cause injury to the tissue. The central vacuum used requires a relatively wide tube making the size and dimensions of the device such that the device is inflexible, and the device, particularly that described by Bilweis, awkward and uncomfortable to use. Critically, the design of the devices with orifices in the suction cup in communication with the operative field, connected to a central external source of vacuum suction allows fluids within the operative cavity to be aspirated and as well, most importantly, allows the aspiration and removal of the insufflating gas within the operative cavity. The latter renders surgery under such conditions difficult at best.

There is thus a widely recognized need for, and it would be highly advantageous to have a grasping device for use in minimally invasive surgery devoid of the above limitations.

SUMMARY OF THE INVENTION

According to the present invention there is provided a surgical grasping instrument, in particular for use by a surgeon in minimally invasive surgery, for grasping, manipulating and moving the tissues and organs of a surgical patient that includes a plurality of suction cups that employ suction produced locally at the site of application.

According to one aspect of the present invention there is provided a surgical instrument for use by a surgeon for grasping a tissue of a surgical patient without causing a crush injury of the tissue, the instrument including: a. an elongate shaft, the shaft having two ends, b. a handle at a first end of the shaft, and c. a grasping tip at a second end of the shaft, the grasping tip including a body, the body housing at least one suction element, wherein the at least one suction element mechanically produces suction locally within the grasping tip.

According to another aspect of the present invention there is provided a method for grasping a tissue of a surgical patient without causing a crush injury to the tissue being grasped, the method including the steps of: a. providing a surgical instrument capable of grasping the tissue without causing a crush injury of the tissue, b. introducing the instrument to an operative site, c. placing the instrument against the tissue to be grasped, d. producing suction distally, locally in the instrument, and, e. grasping the tissue.

According to further features in preferred embodiments of the invention described below, the instrument further includes a power supply for providing electrical power to the at least one suction element.

According to still further features in the described preferred embodiments the handle includes at least one control switch for controlling an operation of the at least one suction element.

According to still further features in the described preferred embodiments the shaft is cylindrical and has a central channel therethrough.

According to still further features in the described preferred embodiments the shaft is constructed from a non-magnetic metal.

According to still further features in the described preferred embodiments the non-magnetic metal is selected from the group consisting of stainless steel and titanium.

According to still further features in the described preferred embodiments the handle, the shaft and the body of the grasping tip are all constructed as parts of a single integral structural piece.

According to still further features in the described preferred embodiments the handle, the shaft and the body of the grasping tip are each constructed as separate individual pieces and connected together.

According to still further features in the described preferred embodiments the grasping tip includes a plurality of the suction elements.

According to still further features in the described preferred embodiments the grasping tip is cylindrical.

According to still further features in the described preferred embodiments the grasping tip has at least one flat longitudinal surface.

According to still further features in the described preferred embodiments the at least one suction element includes: a bell for contact with the tissue to be grasped, the bell having a wall and two ends, a first end closest to the body of the grasping tip, the first end forming a base, and a second end, the second end having a lower surface defining a concavity for the contact.

According to still further features in the described preferred embodiments the bell is fabricated from an elastic material.

According to still further features in the described preferred embodiments the elastic material is a silicone rubber polymer.

According to still further features in the described preferred embodiments the lower surface has a texture element for creating increased friction.

According to still further features in the described preferred embodiments the texture element is selected from the group consisting of ridges, groups, dimples and protuberances.

According to still further features in the described preferred embodiments the suction element further includes a ring within the wall of the bell, the ring made from a magnetically susceptible material.

According to still further features in the described preferred embodiments the magnetically susceptible material is chosen from the group consisting of iron, steel, neodynium, samarium-cobalt, neodynium-iron and neodynium-iron-boron.

According to still further features in the described preferred embodiments the suction element further includes an electromagnet at the base of the bell, whereby the ring is attracted to the electromagnet when the electromagnet is magnetized, causing the lower surface to be drawn toward the base and thereby reducing a volume of the concavity of the lower surface.

According to still further features in the described preferred embodiments the body of the grasping tip further includes an electromagnet within the body, whereby the ring of each of the at least one suction element is attracted to the electromagnet when the electromagnet is magnetized, causing the lower surface of each of the at least one suction element to be drawn toward the body and thereby reducing a volume of the concavity of the lower surface.

According to still further features in the described preferred embodiments the grasping tip further includes a mechanical control element for drawing the lower surface of the bell of each of the at least one suction element toward the base of the bell of each of the at least one suction element and thereby reducing a volume of the concavity of the lower surface.

According to still further features in the described preferred embodiments the grasping tip further includes a mechanical control element for moving the lower surface of the bell of each of the at least one suction element away from the base of the bell of each of the at least one suction element and thereby increasing a volume of the concavity of the lower surface.

According to still further features in the described preferred embodiments the bell is situated within a solenoid core, the base of the bell being a bellows, the lower surface of the bell extending from the core, and wherein the suction element further includes an electromagnetic inductor, the inductor capable of imparting an electromagnetic field upon the core.

According to still further features in the described preferred embodiments the grasping tip is attached to the shaft by a hinge element, whereby the grasping tip is pivotable at an angle in relation to a longitudinal axis of the shaft.

According to still further features in the described preferred embodiments the instrument further includes at least one pivot control element for adjusting the angle.

According to still further features in the described preferred embodiments the instrument is adapted for use in minimally invasive surgery.

According to still further features in the described preferred embodiments the instrument is adapted for use through a surgical instrument selected from the group consisting of an endoscope, a laparoscope, and a bronchoscope.

According to still further features in the described preferred embodiments the instrument is adapted for use for grasping a foreign body.

According to still further features in the described preferred embodiments the method further includes at least one additional step, the additional step chosen from the group consisting of: moving the tissue, manipulating the tissue, releasing the tissue, and applying a surgical lubricant to the instrument.

The present invention successfully addresses the shortcomings of the presently known configurations by providing a surgical grasping instrument, in particular for use by a surgeon in minimally invasive surgery, for grasping and manipulating the tissues and organs of a surgical patient, that avoids crush injury of the tissues, is comfortable to operate, and does not aspirate fluids or insufflating gas from the operative area. Such an instrument allows shorter operative time, requires fewer surgical assistants, and is capable of further reducing the operative complications and allowing faster recovery time. Use of the surgical grasper instrument of the present invention permits performance of more complex surgical procedures on tissues such as liver, ovary and fallopian tubes, or kidney and permits surgery in heretofore difficult circumstances, often in crowded fields with delicate tissue such as in neonatal and pediatric surgery.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1B is an end view of the distal end of a preferred embodiment of a surgical instrument of the present invention;

FIG. 1C is a side view of the distal end of an alternate preferred embodiment of a surgical instrument of the present invention;

FIG. 1D is an end view of the distal end of an alternate preferred embodiment of a surgical instrument of the present invention;

DESCRIPTION OF THE PREFERRED EMBODIMENTS

Figure 1A:
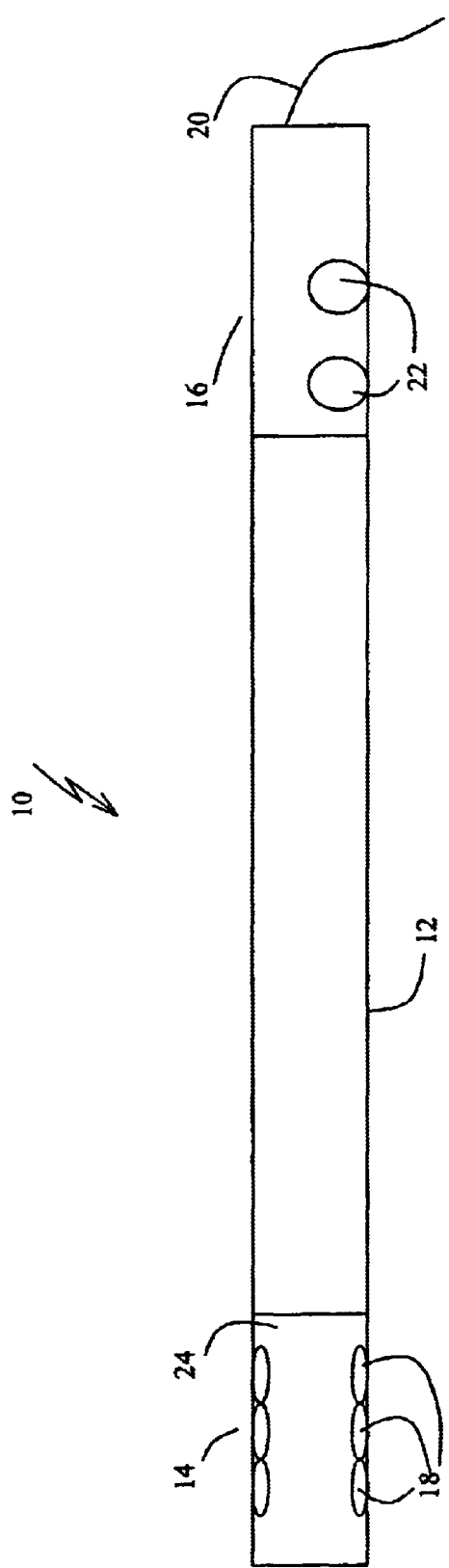
FIG. 1A is a side view of a preferred embodiment of a surgical instrument of the present invention.

The present invention is of a surgical instrument that can be used by a surgeon, in particular in minimally invasive surgery, for grasping, manipulating and moving the tissues and organs of a surgical patient. Specifically, the present invention can be used to grasp the tissues without causing a crush injury to the tissue being grasped.

The principles and operation of a surgical grasping instrument according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. Further, the drawings are diagrammatic and the relative dimensions of the elements illustrated are not to be understood as limiting in any way.

Referring now to the drawings, FIG. 1 illustrates the surgical grasping instrument 10 of the present invention. Grasping instrument 10 is used by a surgeon for grasping, manipulating and moving the tissues and organs of a surgical patient. For the purposes of the specification and accompanying claims, the terms "proximal" and "distal" are used to refer to being near and far respectively from the surgeon operating instrument 10, that is, the part held by the surgeon is the proximal end, and the part of instrument 10 at the surgical site is the distal end.

Grasping instrument 10 essentially comprises an elongated shaft 12, provided with a grasping tip 14 at the distal end and an operating handle 16 at the proximal end. Grasping tip 14 includes at least one, and preferably a plurality of, suction cups 18.

FIG. 1 illustrates a conventional power cord 20, connected to handle 16, used to deliver electrical current to instrument 10. Instrument 10 utilizes standard electrical current as is conventionally supplied in an operating theater and is used by other surgical devices such as electrical knives, cautery and the like. The electrical wiring and circuitry of instrument 10 and all elements of instrument 10 are constructed according to product safety standards for medical and surgical devices, including electrical and electromagnetic standards for shielding and isolation, grounding and insulation, electromagnetic radiation emission, current leakage, shock protection and the like, as is standard in the art. Further, all patient contacting materials used in instrument 10 are biocompatible, and all components of instrument 10 are constructed so as to be either sterilizable by steam, dry heat, or gas sterilization or disposable.

In certain configurations, instrument 10 includes a power supply transformer unit external to instrument 10 to convert standard wall current to an appropriate voltage, current and frequency for delivery to instrument 10 through cord 20. The functions of the electrical system of instrument 10 are discussed in greater detail hereinunder.

Handle 16 further houses at least one control switch 22 for operating instrument 10. Handle 16 is of such dimensions, weight and design as to be comfortably yet tightly grasped with good operative sensitivity, and be easily maneuverable, by the operator thereof. It should preferably be able to be used with one hand by either a left-handed or right-handed surgeon operator thereof. Instrument 10 is designed such that the surgeon can easily, efficiently and comfortable move and manipulate instrument 10 by movements of handle 16 while simultaneously operating control 22, for example, with the tip of a single digit of the hand.

Shaft 12 has a central passage or channel through which traverses electrical wire delivering current to grasping tip 14. Because only electrical wire passes through shaft 12 and shaft 12 does not contain any mechanical components or a vacuum lumen, shaft 12 is capable of being constructed of a narrow diameter, preferably from 5 mm to 15 mm, most preferably about 10 mm. Such a narrow diameter permits operation of instrument 10 using 3 mm, 5 mm, and 10 mm, as are encountered, for example, in neonatal surgery, as well as permitting instrument 10 to be inserted into the operative channel of another device such as a bronchoscope, laparoscope, esophagoscope, endoscope, and the like. Shaft 12 is preferably constructed from a material such as a non-magnetic metal such as stainless steel or titanium. Because shaft 12 has only a central wire traversing therethrough, and is therefore substantially solid, shaft 12 has sufficient rigidity to withstand the forces applied thereto during manipulation and movement.

Handle 16, shaft 12 and housing (or body) 24 of grasping tip 14 in certain preferred embodiments are all constructed as parts of a single integral structural piece, and in other embodiments, handle 16 and grasping tip housing 24 are separate pieces assembled and attached to shaft 12 by any suitable technique known to a person skilled in the art.

Grasping tip 14 is of any shape, including, a circular cylinder, as shown in FIGS. 1A and B, or has at least one flat longitudinal surface (15), as seen in side view in FIG. 1C and in end view in FIG. 1D, as non-limiting examples. Around the circumference of tip 14 is at least one, and preferably, a plurality of suction cups 18. Suction cups 18 are arranged in any geometric configuration on tip 14, such as parallel, symmetrical rows, as a non-limiting example, as illustrated in FIG. 1, or, in other preferred embodiments, are arranged in a non-parallel, asymmetrical, or non-linear configuration or are even randomly placed. In some embodiments suction cups completely surround the circumference of tip 14 and in others only a portion of the surface of tip 14 has cups 18 attached. Different tips 14 with different numbers and configurations of cups 18 are used for different purposes.

Figure 2A:
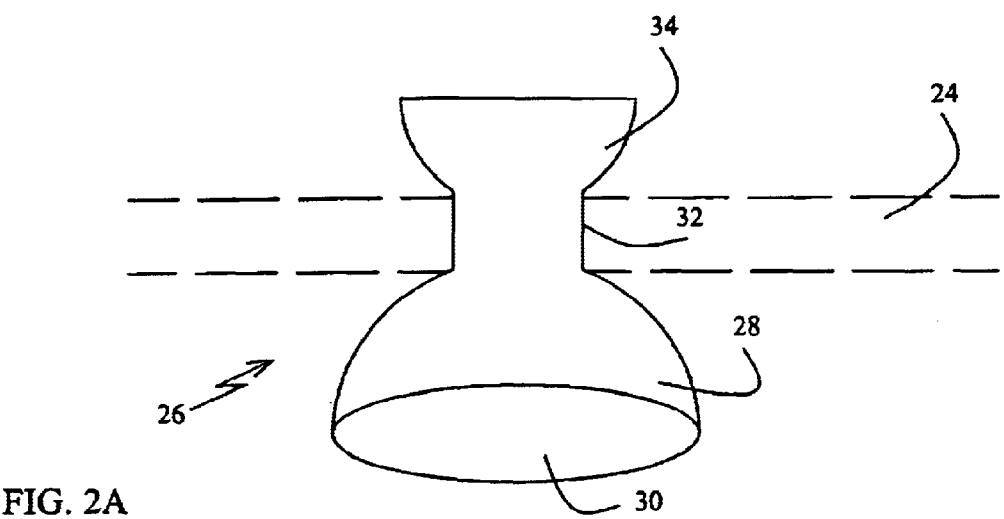
FIG. 2A is a perspective view of a preferred embodiment of a surgical instrument of the present invention.
Figure 2B:
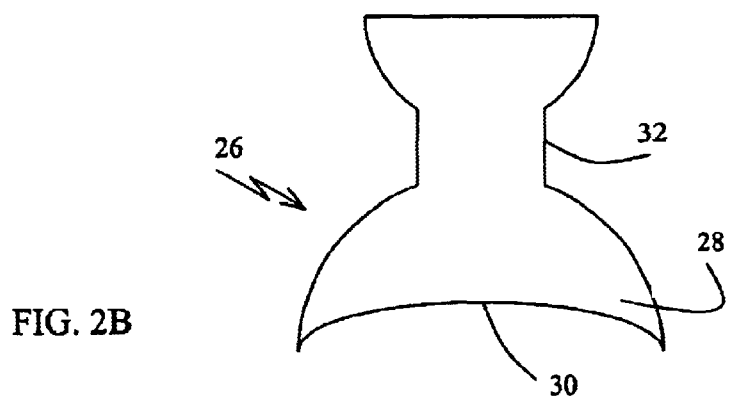
FIG. 2B is a side view of the embodiment of FIG. 2A.
Figure 2C:
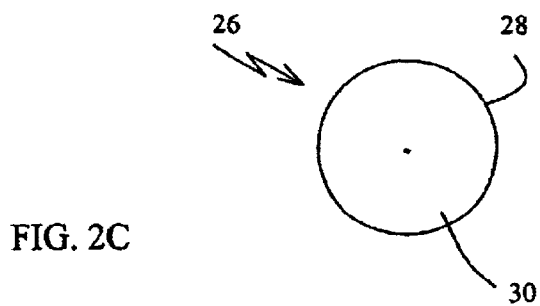
FIG. 2C is a distal end view of the embodiment of FIG. 2A.

FIG. 2 illustrates an individual one of the suction cups 18, the individual suction cup being designated 26 in FIG. 2. Like reference numerals refer to like parts throughout the figures of the drawing. The bell 28 of each suction cup 26 is of the conventional shape and has a concave distal end and distal, lower surface 30 as can be best appreciated in the side view of FIG. 2B. Each suction cup 26 is preferably generally circular as seen best in the distal end view of FIG. 2C; however, in alternate preferred embodiments, an individual suction cup 26 may be of other shapes, in particular, other curved shapes, such as ovoid. Bell 28 is made of a flexible, elastic material, such as preferably, silicone rubber. Alternatively bell 28 is fabricated from another polymer with similar properties to silicone rubber. Lower surface 30 is, in alternative preferred embodiments, smooth, or in other preferred embodiments, textured with a texture element to create a higher friction surface. In various preferred embodiments with a textured lower surface 30, surface 30 alternatively has ridges, grooves, dimples or protuberances of varying patterns. Each of the at least one suction cup 18 is attached to grasper tip housing 24 by any suitable technique known to a person skilled in the art. FIG. 2a illustrates a preferred embodiment in which cup 26 is attached to housing 24 at a site located in the middle of neck 32 of cup 26, however the site of attachment may be proximal or distal to such a site. Each of the at least one suction cup 18 acts to mechanically produce suction locally (at the distal site) and, as opposed to those instruments in the prior art discussed hereinabove, is not in fluid connection to a vacuum lumen or connected to an external source of vacuum suction. Each of the at least one suction cups 18 mechanically generates its own suction locally using electrical power as discussed hereinunder.

Figure 3:
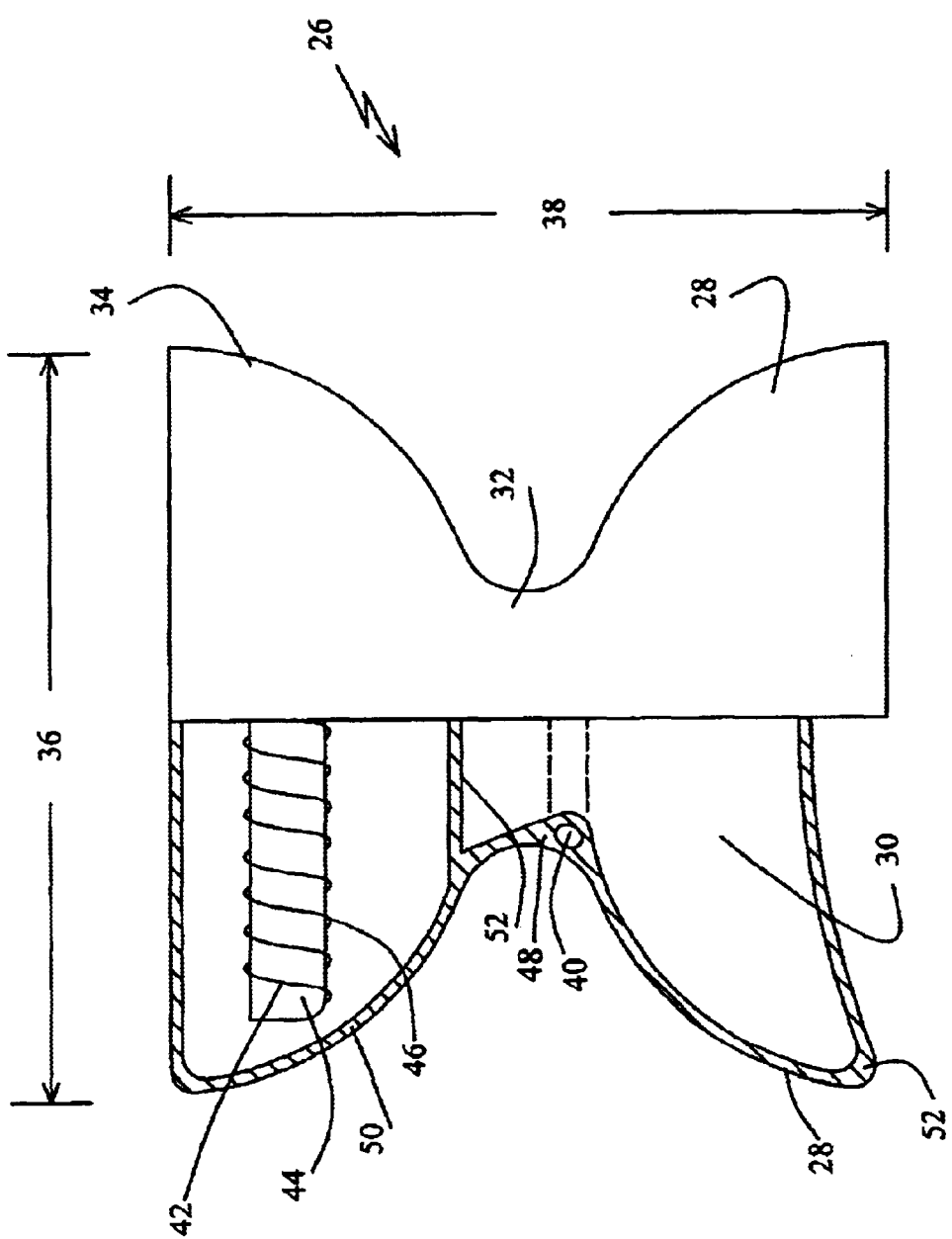
FIG. 3 is a partial cross-sectional side view of a preferred embodiment of a surgical instrument of the present invention.

FIG. 3 is a partial cross sectional view of a preferred embodiment of one of the at least one suction cups 18, again designated as 26. Bell 28 is the distal portion of an integral single piece cup body 50, made preferably from silicone rubber. The diameter 36 of each individual cup of the at least one, and preferably a plurality of, suction cups ranges from 1 mm to 20 mm, preferably from 3 mm to 10 mm and most preferably is 5 mm. The height 38 of each individual cup of the at least one, and preferably a plurality of, suction cups ranges from 3 mm to 10 mm, preferably from 4 mm to 8 mm, and most preferably is 4 mm. It can be appreciated in the cross sectional view of FIG. 3 that the lower surface 30 of bell 28, which extends into neck portion 32, forms a concavity.

On any individual grasping tip 14 there is found at least one suction cup 18. The number of suction cups 18 ranges from 1 to 200, is preferably between 3 and 15 and most preferably is 5 to 10.

Within the wall 48 of bell 28, at the distal limit of the narrowing which constitutes the neck portion 32 (where neck 32 meets bell 28), is embedded a ring 40. Ring 40 is made of a magnetically susceptible material such as metals including iron, steel, or neodymium, or alloys thereof, or rare earth permanent magnetic materials or alloys thereof, such as samarium-cobalt or neodynium-iron-boron. Preferably ring 40 is made of a permanent magnet and is made of neodynium-iron. Wall 48 of neck 32 is highly elastic and acts like a bellows which expands and contracts.

In base 34 (at the end of cup 26 closest to housing 24 of tip 14) of cup 26 is an electromagnet 42, consisting of a ferromagnetic core 44 surrounded by a wire coil 46. When an electric current flows through coil 46, electromagnet 42 becomes magnetized. When electromagnet 42 is magnetized, ring 40 is pulled, that is, attracted to electromagnet 42 and moves closer (proximally) to electromagnet 42, and narrows the concavity formed by lower surface 30. The upward motion of bell 28 draws lower surface 30 inward, reducing the volume of bell 28. The lip 52 of bell 28 is pressed against a surface such as a tissue while electromagnet 42 is energized and lower surface 30 is pulled. Then current flow is stopped, removing the magnetic charge from electromagnet 42 releasing the attraction on ring 40, and allowing bell 28 to passively re-expand due to the elastic recoil of the silicone rubber. As the size of the enclosed space under lower surface 30 expands in volume, vacuum is created. This creates suction against the tissue upon which bell 28 is pressed. In this regard grasper instrument 10 operates in much the same manner as an octopus tentacle, which has a plurality of suckers that suck under the action of circumferential muscles surrounding the sucker. When the magnetic force is applied again the attraction is re-instated, ring 40 returns to its upward position and bell 28 returns to its smaller position, releasing the suction. Thus suction is produced locally and individually (in parallel) in each individual one of the at least one, and preferably, plurality of, suction cups 18. One ordinarily skilled in the art will be capable of operatively assembling such a configuration from commercially available components. Because the power is only on when vacuum is being released or just at the time of application of suction it is applied less than 5% of the time of use of instrument 10 and the heat generated by electromagnet 42 is minimized.

The electrical current that traverses wire coil 46 is capable of being controlled (by the operation of the at least one control switch 22 in handle 16). In certain embodiments, the polarity of the current flow through wire coil 46 (and thus the magnetic field it produces) can be reversed to force (push) ring 40 away to actively help create suction on pressure against the tissue. Control of the suction by simple on/off design of the current flow enables rapid engagement and disengagement of grasping. The design and operative assembly of the electrical circuitry for control and function of electromagnet 42 are done in accordance with principles commonly known to those of ordinary skill in the art to which this invention pertains. Additional components may be required to establish these connections.

The amount of suction generated by each of the at least one, and preferably a plurality of, suction cups 18 is variable and adjustable by varying the elasticity of cup 26 and the dimensions thereof, and ranges from 50 to 300 mm Hg, preferably from 100 to 200 mm Hg, and most preferably is 150 mm Hg. To further enhance the amount of suction applied a lubricant fluid substance can be applied to lower surface 30 of bell 28 of the at least one suction cup 18. This fluid substance can include water, saline, or any sterile surgical lubricant, preferably water soluble, suitable for internal application.

As opposed to conventional graspers which must be maneuvered into position with the forceps jaws placed precisely around the tissue to be grasped, the grasping tip 14 of instrument 10 of the present invention must simply be placed or touched against the tissue to be grasped. Instrument 10 only grasps the surface against which it is touched. Because of the way in which suction is generated, instrument 10 does not aspirate any fluids, including the insufflating air. As discussed hereinabove, different tips 14 with different numbers and configurations of the at least one, and preferably a plurality of, suction cups 18 are used for different purposes. Once the tissue is being held by the suction produced, the tissue can held (including, for example so that the tissue may operated upon by another instrument, as for example, for biopsying the tissue), manipulated, moved (including for example removed), or changed in position. Specifically envisioned as being within the scope of this invention is use of instrument 10 not only to grasp body tissues, but also other materials, such as dressings, surgical materials or foreign bodies. For example, a foreign body lodged in an airway could be removed through a bronchoscope using the grasper instrument 10 of the present invention.

Figure 4:
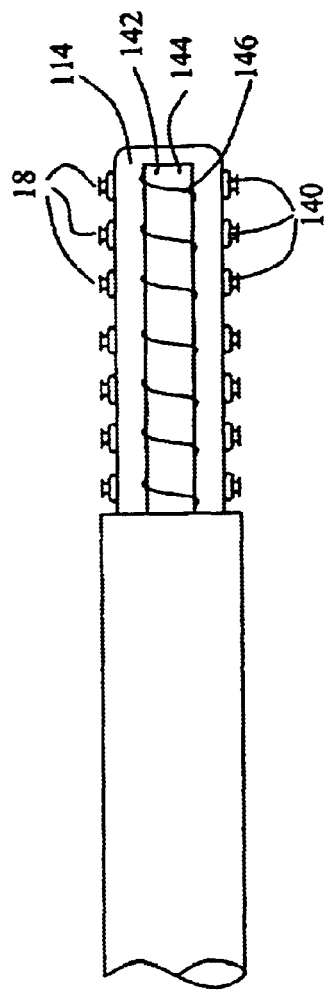
FIG. 4 is a schematic illustration of an alternative preferred embodiment.

In an alternate preferred embodiment, as illustrated in FIG. 4, rather than each of the plurality of suction cups 18 having an individual electromagnet 42 therein, a single central electromagnet 142 with a core 144 surrounded by a coil 146 is located in a central cavity within grasping tip 114. Current flowing through wire coil 146 activates electromagnet 142 which simultaneously attracts each of a plurality of rings 140 circumferentially placed around each of the plurality of suction cups 18. Each of the plurality of suction cups 18 produces its own suction in parallel locally as with the embodiment illustrated in FIG. 3, but under the action of a single electromagnet. In both the embodiments of FIGS. 3 and 4, one of ordinary skills in the art would be able to add systems for cooling the coils if and as necessary. Particularly in such embodiments as those with a central single electromagnet, grasping tip 14 can be made as a disposable, single use attachment, not requiring sterilization.

Figure 5:
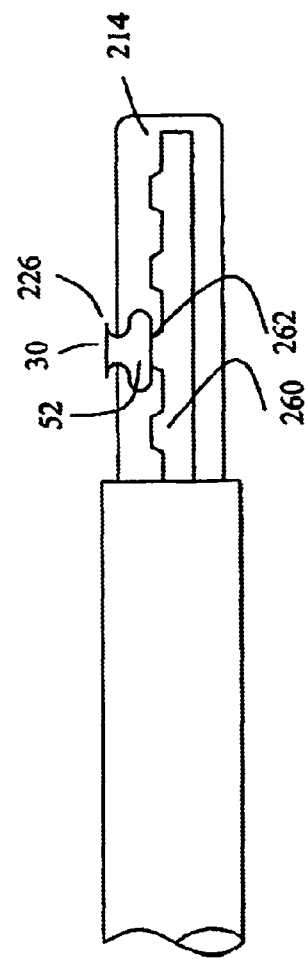
FIG. 5 is a schematic illustration of an alternative preferred embodiment.

FIG. 5 illustrates still another preferred embodiment of the grasper instrument 10 of the present invention. The embodiment illustrated in FIG. 5 operates on a slightly different principle, utilizing a mechanical element to change the volume of the space within the concavity of lower surface 30. In this embodiment rather than a ring circumferentially applied around cup 226, pressure is exerted and released from the rear onto the top of lower surface 30. This can be accomplished by using an electromagnet with a movable central core, operating as solenoid, where the central core can move downward onto the top 52 of lower surface 30, for example. Alternatively, as illustrated in FIG. 5, an axle 260 can be rotated by an electrically activated motor within tip 214. Loop 262 can be tethered to top 52 and can actively pull inward on top 52, (or solenoid core could be attached to top 52 so as to raise it). If cup 226 is placed against tissue after top 52 attached has been pulled inward and held by the loop or by the solenoid core, and then the attraction inward is released, and then the compression is released, because of the elastic recoil of lower surface 30, suction is produced. Alternatively, rotating axle 260 causes loop 262 to be rotated so as press outwards onto the top 52 of lower surface 30. If top 52 of lower surface 30 is compressed once cup 226 has been placed against a tissue, suction will be produced. One ordinarily skilled in the art will be capable of operatively assembling such alternate configurations from commercially available components, including for example, motors, axles and the like.

Figure 6:
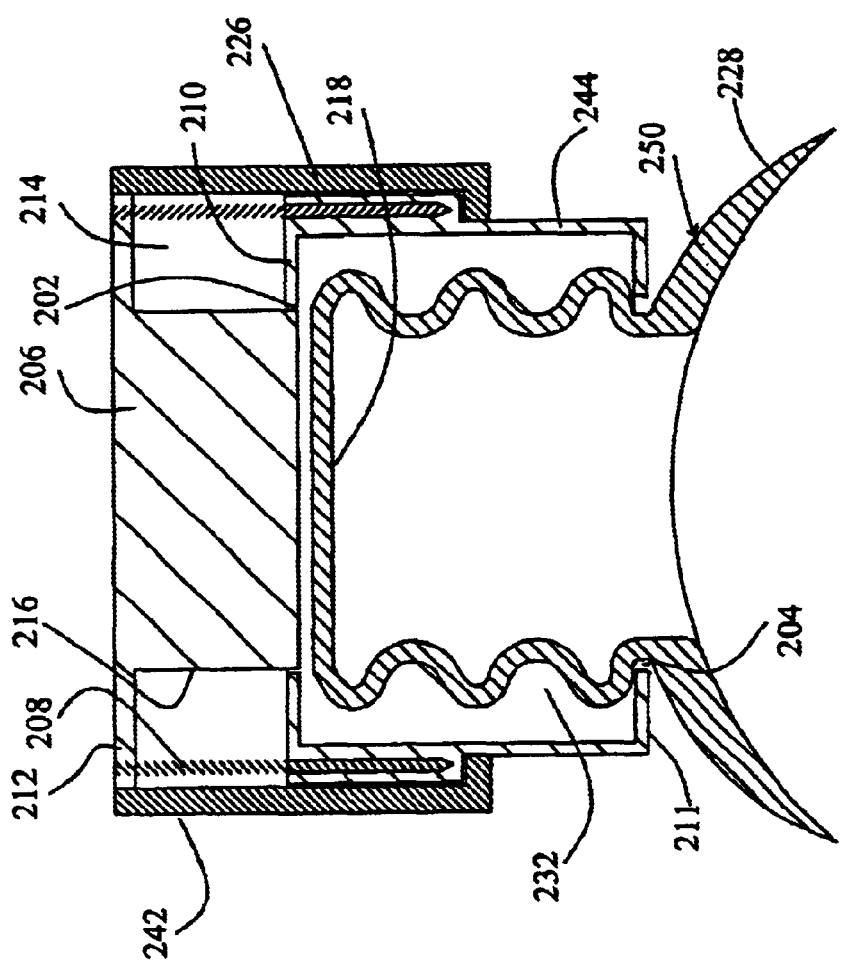
FIG. 6 schematically illustrates a further alternative preferred embodiment; and, FIG. 7 is a schematic illustration of yet an additional alternative preferred embodiment.

FIG. 6 shows yet an additional preferred embodiment of the grasper instrument 10 of the present invention. FIG. 6 illustrates another embodiment of an individual suction cup, here designated 226, one of the at least one suction cups 18. Body 250, is seated within a ferromagnetic metal solenoid core 244, such that neck 232 is enclosed within core 244. There is an opening 202 in the proximal surface 210 of core 244 and another opening, 204, in the distal surface (211). Bell portion 228 of cup body 250 protrudes from opening 204. Neck 232 is formed as a bellows, is highly elastic and is configured to expand and contract. Core 244 itself is seated within electromagnet inductor coil 242 which surrounds core 244. A stopper 206 sits in the proximal portion of coil 242 above the upper or proximal opening 202. Stopper 206 is preferably made from a material such as a rigid plastic and preferably has a "T" shape as illustrated in FIG. 6. At least one spring 208 is in place in the space between the upper surface 210 of core 244 and the cross portion 212 of stopper 206. Preferably the at least one spring 208 is a plurality of springs situated around the inner perimeter of the central cavity 214 within coil 242. When current is applied to coil 242, core 244 rises within cavity 214. Neck bellows 232 contracts and is compressed by the protruding portion 216 of stopper 206 against the upper surface 218 of cup body 250.

Bell 250 is then placed against the tissue to be grasped. The current flow to coil 242 is stopped and the attraction on core 244 is released. The at least one spring 208 acts to push back on core 244 causing neck 232 to expand while being pressed up against the tissue. The increase in volume within bell 228 causes suction against the tissue to be grasped. Current flow to coil 242 again will release the suction.

Figure 7:
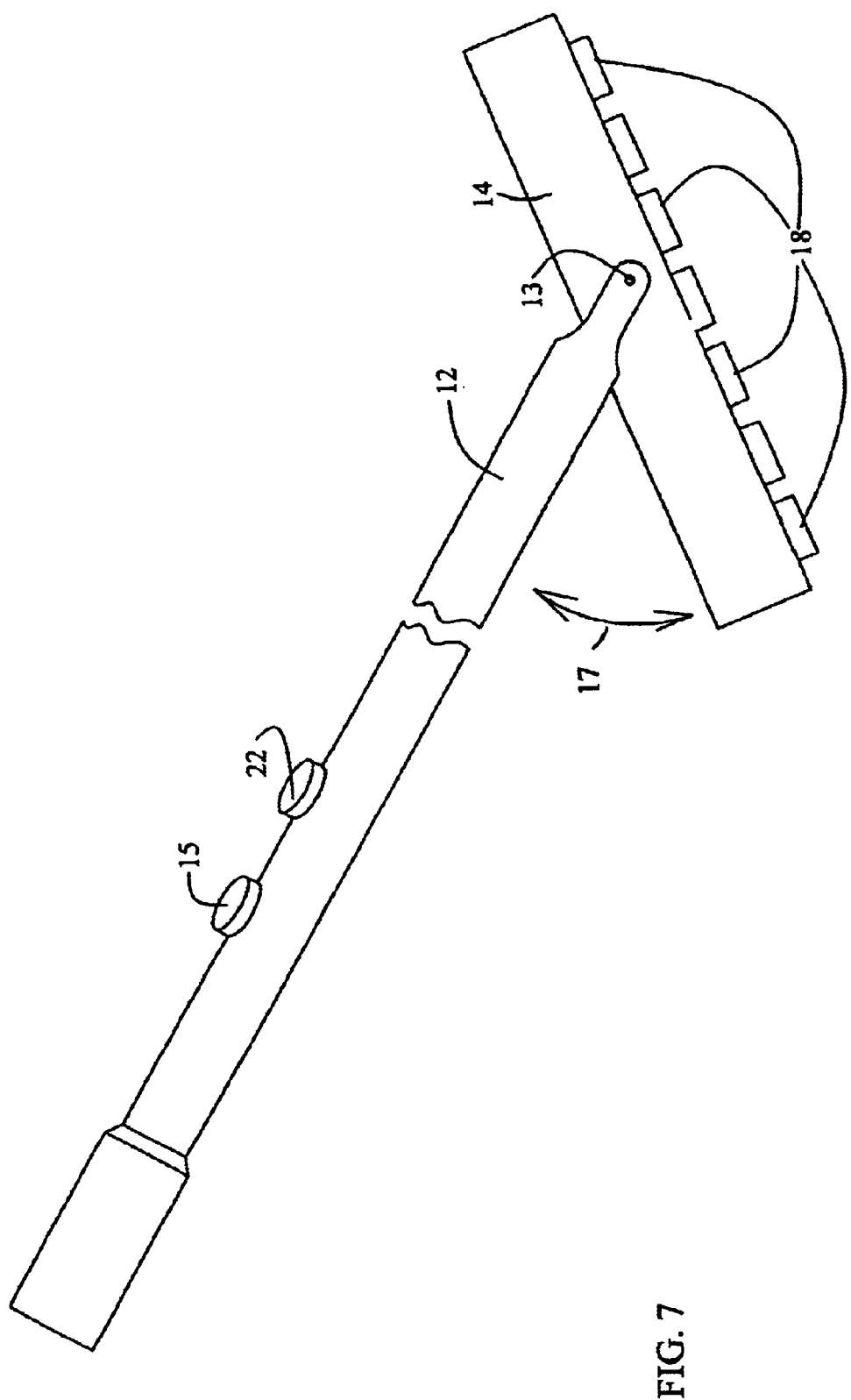

FIG. 7 illustrates a further preferred embodiment of grasper instrument 10. In this embodiment grasping tip 14 is pivotable, at any angle [indicated by 17] (preferably from 0 degrees to 90 degrees) in relation to the longitudinal axis of shaft 12, around a hinge of attachment 13 to shaft 12. Electrical or mechanical mechanisms including such elements as cables, gears and activating controls (e.g., 15) (such as a switch or joystick) are supplied within shaft 12 and tip 14 to control the position of tip 14 relative to shaft 12, thereby adjusting angle 17. For example, at the time of insertion of instrument 10 through a surgical port, the position of tip 14 can be placed parallel or nearly parallel to shaft 12. Then once instrument 10 is in place at the operative site, tip 14 can be rotated so as to be perpendicular to shaft 12 for use in grasping, moving and manipulating tissues and objects. If shaft 12 is fixed in place manipulating tip 14 with joystick controls to move tissues is possible, reducing the number of surgical assistants required for surgery.

The above described surgical instrument will find use primarily in conjunction with a method for grasping, manipulating and moving the tissues and organs of a surgical patient that can be used by a surgeon, in particular in minimally invasive surgery. Specifically, such a method can be used to grasp the tissues without causing a crush injury to the tissue being grasped.

According to the present invention, such a method includes the steps of: (a) providing a surgical grasping instrument (10) capable of grasping the tissue without causing a crush injury to the tissue being grasped, (b) introducing the instrument to the operative site, (c) placing the instrument against the tissue surface to be grasped, (d) distally and locally producing suction in the instrument, and (e) grasping the tissue. The method can further include the steps of moving the tissue, manipulating the tissue and releasing the tissue. Further the method can include the steps of applying a surgical lubricant substance to the instrument, or of introducing the instrument through another instrument such as a bronchoscope, laparoscope or endoscope or through a port for minimally invasive surgery. In addition, in alternative embodiments of the method of the present invention, specifically envisioned as being within the scope of this invention is use of instrument 10 not only to grasp body tissues, but also other materials, such as dressings, surgical materials or foreign bodies. For example, a foreign body lodged in an airway could be removed through a bronchoscope using the grasper instrument 10 and method of the present invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A surgical instrument for use by a surgeon for grasping a tissue of a surgical patient without causing a crush injury of the tissue, the instrument comprising: a. an elongate shaft, said shaft having two ends, b. a handle at a first end of said shaft, and c. a grasping tip at a second end of said shaft, said grasping tip including a body, said body housing at least one suction element, wherein said at least one suction element mechanically produces suction locally within said grasping tip.

2. The instrument of claim 1, further including a power supply for providing electrical power to said at least one suction element.

3. The instrument of claim 1, wherein said handle includes at least one control switch for controlling an operation of said at least one suction element.

4. The instrument of claim 1, wherein said shaft is cylindrical and has a central channel therethrough.

5. The instrument of claim 1, wherein said shaft is constructed from a non-magnetic metal.

6. The instrument of claim 5, wherein said non-magnetic metal is selected from the group consisting of stainless steel and titanium.

7. The instrument of claim 1, wherein said handle, said shaft and said body of said grasping tip are all constructed as parts of a single integral structural piece.

8. The instrument of claim 1, wherein said handle, said shaft and said body of said grasping tip are each constructed as separate individual pieces and connected together.

9. The instrument of claim 1, wherein said grasping tip includes a plurality of said suction elements.

10. The instrument of claim 1, wherein said grasping tip is cylindrical.

11. The instrument of claim 1, wherein said grasping tip has at least one flat longitudinal surface.

12. The instrument of claim 1, wherein said at least one suction element includes: a bell for contact with the tissue to be grasped, said bell having a wall and two ends, a first end closest to said body of said grasping tip, said first end forming a base, and a second end, said second end having a lower surface defining a concavity for said contact.

13. The instrument of claim 12, wherein said bell is fabricated from an elastic material.

14. The instrument of claim 13, wherein said elastic material is a silicone rubber polymer.

15. The instrument of claim 12, said lower surface having a texture element for creating increased friction.

16. The instrument of claim 15, wherein said texture element is selected from the group consisting of ridges, groups, dimples and protuberances.

17. The instrument of claim 12, wherein said suction element further includes: a ring within said wall of said bell, said ring made from a magnetically susceptible material.

18. The instrument of claim 17, wherein said magnetically susceptible material is chosen from the group consisting of iron, steel, neodynium, samarium-cobalt, neodynium-iron and neodynium-iron-boron.

19. The instrument of claim 17, wherein said suction element further includes: an electromagnet at said base of said bell, whereby said ring is attracted to said electromagnet when said electromagnet is magnetized, causing said lower surface to be drawn toward said base and thereby reducing a volume of said concavity of said lower surface.

20. The instrument of claim 17, wherein said body of said grasping tip further includes: an electromagnet within said body, whereby said ring of each of said at least one suction element is attracted to said electromagnet when said electromagnet is magnetized, causing said lower surface of each of said at least one suction element to be drawn toward said body and thereby reducing a volume of said concavity of said lower surface.

21. The instrument of claim 12, wherein said bell is situated within a solenoid core, said base of said bell being a bellows, said lower surface of said bell extending from said core, and wherein said suction element further includes an electromagnetic inductor, said inductor capable of imparting an electromagnetic field upon said core.

22. The instrument of claim 1, wherein said grasping tip is attached to said shaft by a hinge element, whereby said grasping tip is pivotable at an angle in relation to a longitudinal axis of said shaft.

23. The instrument of claim 22, further including at least one pivot control element for adjusting said angle.

24. The instrument of claim 1, wherein the instrument is adapted for use in minimally invasive surgery.

25. The instrument of claim 1, wherein the instrument is adapted for use through a surgical instrument selected from the group consisting of an endoscope, a laparoscope, and a bronchoscope.

26. The instrument of claim 1, wherein the instrument is adapted for use for grasping a foreign body.

* * * * *